United States Patent [19]

Oyama

[11] 4,313,937
[45] Feb. 2, 1982

[54] METHOD FOR PRODUCING LONG-LASTING ANALGESIC EFFECTS OF β-ENDORPHIN

[76] Inventor: Tsutomu Oyama, 31, Zaifu-cho, Hirosaki, Aomori, Japan

[21] Appl. No.: 178,571

[22] Filed: Aug. 12, 1980

[51] Int. Cl.³ .................................................. A61K 37/00
[52] U.S. Cl. ..................................................... 424/177
[58] Field of Search .................. 260/112.5 R; 424/177

[56] References Cited

U.S. PATENT DOCUMENTS

| | | | |
|---|---|---|---|
| 4,038,222 | 7/1977 | Li | 424/177 |
| 4,098,778 | 7/1978 | Li | 424/177 |
| 4,116,950 | 9/1978 | Li | 424/177 |
| 4,219,468 | 8/1980 | Li | 260/112.5 R |

OTHER PUBLICATIONS

Saunders, Medical Dictionary p. 78.
"The Merck Manual" (1977) pp. 2026–2029.

*Primary Examiner*—Delbert R. Phillips
*Attorney, Agent, or Firm*—Berman, Aisenberg & Platt

[57] ABSTRACT

Profound and long-lasting analgesia is produced by infusing β-endorphin or a physiologically acceptable salt thereof into the subarachnoid space of the spinal cord or the epidural space of the spinal cord.

5 Claims, No Drawings

METHOD FOR PRODUCING LONG-LASTING ANALGESIC EFFECTS OF β-ENDORPHIN

This invention relates to a method for producing long-lasting analgesia in patients. More particularly, this invention relates to a method for producing long-lasting analgesia in man which comprises infusing β-endorphin or a physiologically acceptable salt thereof into the subarachnoid or epidural space of the spinal cord as well as a method for prolonging the analgesic action of β-endorphin and its salts.

β-Endorphin is a fragment of β-lipotropin (LPH) which is a pituitary hormone. This peptide fragment (i.e. β-endorphin) is composed of 31 amino acid units and possesses morphine-like activity. Its total synthesis has already been accomplished [J. Med. Chem., 20, 325 (1977)].

This compound is not only a morphine agonist but also has useful pharmacological actions, such as the action to regulate pituitary hormone secretion and information activity, and, therefore, has been known to have a great deal of potential as the best possible analgesic of the twentieth century. Under the circumstances, many workers have been trying to develop clinical uses for β-endorphin but their efforts are still in experimental stages and no success has been reported in the practical application of the potentially useful pharmacological activities of this compound.

By way of illustration, when β-endorphin is intravenously or intramuscularly administered to man and laboratory animals, no statistically significant analgesia was obtained in any case. [Commun. in Psychopharmacol., 1, 493–500 (1977)]. The presumed cause is the existence of the blood-brain barrier or the existence of certain decomposing enzymes in the blood. Thus, β-endorphin does not display its effects at all on administration by the usual oral and parenteral routes. For this reason, an attempt was made to infuse β-endorphin directly into the cerebral ventricle of the patent. [Commun. in Psychopharmacol., 2, 33–37 (1978)]. However, this practice causes the compound to exert its direct primary pharmacological action to be felt in the brain so that it induces various undersirable side effects in addition to the desired pain relief as the compound acts on various nerves. Therefore, when the intracerebral route of administration is chosen, it is necessary to constantly watch responses of the patient and adjust the dose and other factors to prevent onset of side effects. Furthermore, the administration of β-endorphin into the cerebral ventricle provides only a very short-term relief of pain, e.g. lasting only 10 to 15 hours at the maximum. Therefore, when long-lasting analgesia is necessary, for example after surgery, a single dose is insufficient and a complicated therapeutic regimen must be employed. Moreover, the most serious problem which is encountered when β-endorphin is administered into the cerebral ventricle is that it is necessary to create an opening in the skull for infusion of the medicament and this has been a major roadblock to clinical application of β-endorphin.

For example, in such intracerebral administration of β-endorphin for the treatment of general intractable headache, parturient pain, peri and postoperative pain, the surgical intervention for making an opening in the skull to infuse β-endorphin is too grave a stress for the debilitated or emaciated patient to tolerate, thus, β-endorphin therapy is nearly impossible in such cases. Moreover, direct administration of β-endorphin into the cerebral ventricle means its direct action on the brain, and its side effects have untoward influences on patients who are already in a seriously morbid or weakened condition. For obstetrical, intra or postoperative analgesia, it is not practical to administer β-endorphin through a bur hole of the skull.

The present inventor's research was concentrated on the development of a clinically useful method for administration of β-endorphin. The research led to the discovery that, by using the subarachnoid space of the spinal cord or the epidural space of the spinal cord as the site of administration, the pain-relieving effect of βendorphin may be brought into being through an entirely different mechanism, i.e. different from that involved in administration by the conventional routes, with consequent longer-lasting analgesia.

Thus, the invention is directed to a method for producing analgesia in man which comprises infusing β-endorphin or a physiologically-acceptable salt thereof into the subarachnoid or epidural space of the spinal cord, thereby causing the primary pharmacological action of the compound to be felt on the opiate receptors of the spinal cord and cerebrum so as to produce the desired analgesia.

Further, this invention is directed to a method for prolonging the analgesic action of β-endorphin and its salts through infusing β-endorphin or its salt into the subarachnoid or epidural space of the spinal cord.

It is therefore an object of this invention to provide a method for producing analgesia in man.

It is another object to provide a method for prolonging the analgesic action of β-endorphin and a physiologically acceptable salt thereof.

Other objects of this invention will become apparent from the following description and claims.

The method of this invention is applicable to patients who need removal or relief of pain, and is especially suitable for application to pain-afflicted patients for whom narcotics have heretofore been the only useful remedy, such as the patients in postoperative period or in the terminal stage of cancer. The object of painless labor can also be accomplished by applying the method of this invention to obsteric patients.

In accordance with this invention, both chemically synthesized β-endorphin and naturally-occurring β-endorphin, such as the β-endorphin obtained by decomposition of LPH or by genetic engineering, can be employed with equal success. Such β-endorphin may be used in the free form or as a physiologically-acceptable salt thereof, e.g. such acid-addition salts as the corresponding mineral acid salts (e.g. hydrochloride, sulfate, etc.) and organic acid salts (e.g. acetate, citrate, tartrate, etc.). Among the above-mentioned salts, the acetate is particularly beneficial.

β-Endorphin or a salt thereof is generally used as an injectable preparation. Such an injectable product can be prepared by the established pharmaceutical procedure. For example, β-endorphin or its salt is dissolved in a suitable medium, such as physiological saline, and the solution is heat-sterilized. An alternative procedure may comprise dissolving β-endorphin or its salt in an aqueous solution of carbohydrate (e.g. glucose, sorbitol or mannitol) and lyophilizing the solution for extemporaneous use.

The dosage of β-endorphin can be selected according to the degree of pain and other condition of the patient. Generally the recommended dosage is about 0.1 to 5 mg (as dried free β-endorphin; the same applies hereinafter)/adult patient/dose, and preferably about 0.5 to 3 mg/adult patient/dose.

The infusion into the subarachnoid space of the spinal cord can be performed by the technique of lumbar anesthesia which is known per se. Generally, it is preferable to perform a puncture between the second and third lumbar vertebrae and infuse the drum into the subarachnoid space of the spinal cord.

For infusion into the epidural space of the spinal cord, one may follow the technique of epidural anesthesia or sacral anesthesia which is known per se.

In accordance with this invention, the fear of onset of the side effects of β-endorphin is eliminated and a selective analgesic effect can be easily obtained. Moreover, the pharmacological action of this compound is rendered mild and the desired mild anesthesia and sedation are obtained. Thus, the method of this invention ensures sustained β-endorphin effects over a longer period, i.e. 22 to 74 hours after administration.

Thus, the method of this invention ensures a substantially immediate complete relief of pain which continues for a prolonged period, substantially without inducing side effects such as in the respiratory, circulatory or central nervous system, thus being believed to contribute considerably to therapeutic medicine.

The following clinical examples are further illustrative of this invention but should not be considered to be limitative of the scope of the invention.

CLINICAL EXAMPLES

Twenty-three patients with chronic intractable pain in the back, chest, abdomen, rectum and/or thigh regions secondary to metastatic malignancies were selected for this test.

Systemically-administered analgesics had not completely suppressed the pain when given at reasonable dose levels and frequency; the patients usually had not slept well because of their pain. The protocol was explained to them, and informed consent was obtained. Systemic analgesics were withheld for at least 5 hours before administration of β-endorphin. Neurological examinations and electroencephalography (EEG) were performed immediately before and every 2 hours after the injection of β-endorphin. The visual pain scale ("Adv. Neurol.", 1974, 4, 281-283) was explained to each patient; baseline pain intensity was determined 30 min. before the injection.

β-Endorphin acetate used here was prepared to high purity according to the method described in the Biochem. Biophys. Res. Commun., 74, 248-255 (1977). β-Endorphin acetate, 3 mg (equivalent to 2.5 mg of dried free β-endorphin) with 150 mg of glucose and 3 ml of distilled water (in 8 patients, cases 1-8) or with 3 ml of physiological saline and no glucose (in 7 patients, cases 9-15), was injected into the subarachnoid space (cases 1-14) or epidural space (case 15) of the spinal cord by lumbar puncture between the 2nd and 3rd lumbar vertebrae. After the injection of β-endorphin acetate, the intensity of pain, vital signs, central-nervous-system examination, EEG, electrocardiogram (ECG), pulse rate, respiratory rate, blood-gas analysis, and body temperature were monitored. Simple behavioural parameters were also observed.

In a single-randomization design, three physicians administered successively β-endorphin acetate injection or physiological saline (as a placebo) in random order to 5 patients (cases 9-12, 14). All other patients received only β-endorphin acetate, without placebo.

For the purpose of comparison, β-endorphin acetate was injected intramuscularly (cases 18-20), intravenously (cases 16 and 17), and intracerebrally (cases 20-23).

In this test, all the injections of β-endorphin to patients were sterilized through Millipore filter.

Results

All 15 patients, who were injected β-endorphin acetate into the subarachnoid space or epidural space of the spinal cord, reported complete relief of pain. In 13 patients among the above mentioned 15 patients, pain disappeared in 1-5 min. after the injection of β-endorphin acetate. The pain relief after the injection continued for 22.5 to 73.5 hours (average: 33.4 hours). No objective effect of the placebo except temporary effect was observed in all 5 patients.

The injection of β-endorphin acetate into the subarachnoid space or epidural space of the spinal cord caused no discomfort to all the patients. The 12 of 15 patients became drowsy for 1-4 hours after injection. The eight patients slept, and one patient of the 8 patients (case No. 5) slept fo 80 min. in 40 min. after the injection. The one patient (case No. 7) continued to sleep for 110 min. in 10 min. after the injection. The other 6 patients slept for 1-2 hours. All the patients were easily arousable by verbal stimuli. No signs of respiratory depression, arterial blood-gas changes, nausea, hypotension, hypothermia, catatonia, or muscle rigidity were observed. All patients slept well at night, except for one patient (case No. 13) who had extensive ascites at the time of the test. During the period of pain relief, perception of venepuncture and light touch remained intact. No abnormalities in the ECG or EEG were observed during the procedure.

In 2 patients who were injected β-endorphin acetate intravenously, one patient reported no analgesic effect, and another one patient reported the analgesic effect of only one hour duration, which was considered to be placebo effect.

In 3 patients who were injected β-endorphin acetate intramuscularly, 2 patients reported no analgesic effect, and another one patient reported placebo effect only for one hour.

The relief of pain in all 3 patients, who were injected β-endorphin into cerebral ventricle continued only for 8-12 hours.

The above results show that the method of the present invention is excellent.

The results of this test are shown in Table 1.

TABLE 1

| Patient no. | Age | Sex | Body-weight (kg) | Previous analgesics (dose [mg] and no. of doses/day) | Pain relief after β-endorphin or placebo | | Remarks |
| --- | --- | --- | --- | --- | --- | --- | --- |
| | | | | | Onset (min.) | Duration (h.) | |
| 1 | 57 | M | 65 | Pentazocine 15 × 2-3 | 5 | 27 | Somnolence, disorientation? |

TABLE 1-continued

| Patient no. | Age | Sex | Body-weight (kg) | Previous analgesics (dose [mg] and no. of doses/day) | Pain relief after β-endorphin or placebo | | Remarks |
|---|---|---|---|---|---|---|---|
| | | | | | Onset (min.) | Duration (h.) | |
| | | | | Aminopyrin, Mefenamic acid 500 × 3 | | | |
| 2 | 29 | M | 65 | Pentazocine 30 × 4-5 | 5 | 27½ | Somnolence |
| 3 | 48 | F | 40 | Meperidine 35 4 Pentazocine 30 × 3 | 4 | 26½ | Somnolence to sleep |
| 4 | 68 | M | 45 | Pentazocine 15 × 6 | 5 | 29½ | Somnolence to sleep, disorientation? |
| 5 | 39 | F | 41 | Pentazocine 30 × 5 Indomethacin 50 × 2 | 1 | 24 | Sleep |
| 6 | 43 | M | 55 | Pentazocine 30 × 5 Indomethacin 50 × 1 | 2 | 36 | Somniloquy |
| 7 | 49 | F | 33 | Pentazocine 30 × 5 Hydroxyzine 50 × 5 | 4 | 25½ | Euphoria, sleep, somniloquy, disorientation? |
| 8 | 43 | M | 54 | Pentazocine 15 × 2 Indomethacin 50 × 1 | 2 | 28½ | Somnolence |
| 9 | 67 | F | 43 | Meperidine 35 × 4 (for 1 yr. 8 mon.) | 16 (—)* | 24 (—)* | Sleep |
| 10 | 50 | M | 46 | Indomethacine 50 × 1 (for 3 mo.) | 2 (5)* | 25 (½)* | Sleep |
| 11 | 62 | M | 45 | Pentazocine 15 × 4-5 (for 5 mo.) | 2 (—)* | 47 (—)* | Sleep, euphoria |
| 12 | 47 | M | 54 | Pentazocine 15 × 4-5 Diazepam (for 1 yr. 2 mo.) | 2 (—)* | 73½ (—)* | Sleep |
| 13 | 33 | M | 65 | Meperidine 17.5 × 6 (for 6 mo.) | 2 | 51 | Somnolence |
| 14 | 30 | M | 53 | Pentazocine 15 × 4-5 Hydroxyzine 25 × 2-3 (for ½ mo.) | 2 (3)* | 22½ (4)* | Euphoria, somnolence to sleep |
| 15 | 56 | M | 45 | Pentazocine 15 × 4-6 (for 6 mo.) | 2 | 68 | Sleep |
| 16 | 48 | F | 43 | Meperidine 17.5 × 6 (for 6 mo.) | 3 | 1 | |
| 17 | 70 | M | 40 | Pentazocine 15 × 4-5 (for 1 yr. 1 mo.) | 0 | 0 | |
| 18 | 49 | F | 55 | Pentazocine 30 × 5 (for 4 mo.) | 0 | 0 | |
| 19 | 62 | F | 48 | Meperidine 35 × 4 (for 1 yr. 3 mo.) | 0 | 0 | |
| 20 | 65 | M | 49 | Pentazocine 30 × 5 (for 6 mo.) | 15 | 1 | |
| 21 | 45 | M | 40 | Meperidine 17.5 × 5 (for 8 mo.) | 3 | 10 | |
| 22 | 67 | M | 42 | Pentazocine 30 × 4 (for 7 mo.) | 4 | 12 | |

TABLE 1-continued

| Patient no. | Age | Sex | Body-weight (kg) | Previous analgesics (dose [mg] and no. of doses/day) | Pain relief after β-endorphin or placebo | | Remarks |
|---|---|---|---|---|---|---|---|
| | | | | | Onset (min.) | Duration (h.) | |
| 23 | 63 | M | 48 | Meperidine 35 × 4 (for 1 yr) | 3 | 8 | |

*Placebo

What is claimed is:

1. A method for producing analgesia in man which comprises infusing β-endorphin or a physiologically-acceptable salt thereof into the subarachnoid space of the spinal cord or the epidural space of the spinal cord.

2. A method as claimed in claim 1, in which a sufficient amount of β-endorphin or a physiologically-acceptable salt thereof to cause the primary pharmacological action of said compound to react on the opiate receptors of the spinal cord and the cerebrum is infused.

3. A method as claimed in claim 1, in which the physiologically-acceptable salt is acetate.

4. A method as claimed in claim 1, in which β-endorphin or a physiologically-acceptable salt thereof is in the form of an injectable preparation.

5. A method for prolonging the analgesic action of β-endorphin or a physiologically-acceptable salt thereof, which comprises infusing β-endorphin or a physiologically-acceptable salt thereof into the subarachnoid space of the spinal cord or the epidural space of the spinal cord.

* * * * *